United States Patent
Bloom et al.

(10) Patent No.: US 6,863,833 B1
(45) Date of Patent: Mar. 8, 2005

(54) MICROFABRICATED APERTURES FOR SUPPORTING BILAYER LIPID MEMBRANES

(75) Inventors: David M. Bloom, Wilson, WY (US); Mark C. Peterman, Stanford, CA (US); Jonathan M. Ziebarth, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 10/177,330

(22) Filed: Jun. 21, 2002

Related U.S. Application Data (60) Provisional application No. 60/301,972, filed on Jun. 29, 2001.

(51) Int. Cl.[7] .............................. B82B 1/00; B82B 3/00
(52) U.S. Cl. ............................ 216/2; 216/39; 216/56; 216/57; 216/79; 216/99; 204/403.08; 204/516; 204/518; 436/71; 436/72; 427/2.23; 427/245
(58) Field of Search .............................. 216/2, 39, 56, 216/57, 79, 99, 27, 41, 51, 49; 427/2, 13, 245; 436/71, 72; 435/288.5; 204/403.08, 516, 518, 418

(56) References Cited

U.S. PATENT DOCUMENTS

| | | | | |
|---|---|---|---|---|
| 4,612,554 A | * | 9/1986 | Poleshuk | 347/63 |
| 5,154,815 A | * | 10/1992 | O'Neill | 205/75 |
| 5,187,066 A | * | 2/1993 | Becker et al. | 435/7.36 |
| 5,756,879 A | * | 5/1998 | Yamagishi et al. | 73/28.01 |
| 5,798,030 A | * | 8/1998 | Raguse et al. | 204/403.08 |
| 6,500,571 B2 | * | 12/2002 | Liberatore et al. | 429/2 |
| 6,503,452 B1 | * | 1/2003 | Boxer et al. | 422/82.02 |
| 2002/0006357 A1 | * | 1/2002 | McGeoch et al. | 422/82.01 |
| 2003/0062657 A1 | * | 4/2003 | Parameswaran et al. | 264/553 |
| 2003/0077642 A1 | * | 4/2003 | Fritsch et al. | 435/6 |
| 2003/0102263 A1 | * | 6/2003 | Lopez et al. | 210/639 |

OTHER PUBLICATIONS

60/268365.*
60/240691.*
Steven G. Boxer "Molecular transport and organization in supported lipid membranes" Model Systems pp. 704–709.
Anette Stromberg et al. "Microfluidic Device for Combinatorial Fusion of Liposomes and Cells" Analytical Chemistry 73(1):126–130 (Jan.2001).
Ming C. Wu "Micromachining for Optical and Optoelectronic Systems" Proceedings of the IEEE, 85(11):1833–1856 (Nov. 1997).

* cited by examiner

Primary Examiner—Allan Olsen
(74) Attorney, Agent, or Firm—Lumen Intellectual Property Services, Inc.

(57) ABSTRACT

The invention provides microfabricated silicon substrates and devices having extremely small apertures (termed "nanoapertures") and methods for producing such nanoapertures. The devices have a nanoaperture (which may have a diameter ranging from about a few millimeters to as small as a few nm) across a substrate effective to connect two regions separated by the substrate. The devices are suitable for the formation of lipid bilayer membranes across the apertures, and for use in devices such as biosensors. Substrates and devices may include multiple nanoapertures, which may each support a lipid bilayer membrane, allowing fault tolerant devices such as fault-tolerant biosensors, and allowing devices able to sense more than one target molecule.

42 Claims, 7 Drawing Sheets

MICROFABRICATED APERTURES FOR SUPPORTING BILAYER LIPID MEMBRANES

CROSS REFERENCES

This application claims priority from and incorporates by reference in its entirety U S. Provisional Application Ser. No. 60/301,972, titled "Microfabricated Apertures For Supporting Bilayer Lipid Membranes", by David Bloom et al., filed Jun. 29, 2001.

FIELD OF THE INVENTION

The invention pertains to microfabricated apertures, methods for forming microfabricated apertures, and devices having microfabricated apertures.

BACKGROUND OF THE INVENTION

Small-sized apertures find use in a variety of applications including scanning microscopes, ink-jet nozzles, and micromechanical systems. Small apertures are often made using microfabrication techniques. Microfabrication techniques and applications may be found, for example, in U.S. Pat. No. 5,517,280 to Quate, U.S. Pat. No. 5,858,256 to Minne et al., U.S. Pat. No. 5,943,075 to Lee et al., and U.S. Pat. No. 6,219,015 to Bloom. All patents, both supra and infra, are hereby incorporated by reference in their entirety.

For example, microfabrication techniques are used in the manufacture of semiconductor components. The most common microfabrication technique is photolithography, in which photoresist layers on a substrate are exposed to radiation and so made more resistant to chemical processes that are to be applied later to the substrate. In this way, specific regions of the substrate may be removed or altered by chemical action while neighboring regions are not removed or altered. A photoresist pattern may be formed by a photomask made from masking material placed in a pattern on a substrate by a stamp, by sputtering, by optical methods, or by other means. Typically, a photomask is used to block irradiation of some regions while allowing other regions of the substrate surface to be irradiated by light in order to produce a desired pattern of resistant and susceptible regions. Features of such patterns produced by ultraviolet radiation may be as small as about 0.5 $\mu$m. However, features smaller than about 0.5 $\mu$m cannot generally be formed by these techniques.

Artificial lipid bilayer membranes (ALBMs) are membranes formed with phospholipids and sometimes solvents that mimic many of the properties of biological membranes. ALBMs may be formed across small apertures (that are nevertheless typically larger than cells or cellular organelles). Solvent-containing membranes, which differ from living membranes by including solvents such as decane or hexadecane, may be formed across apertures in hydrophobic materials such as polytetrafluoroethylene (Teflon®), polystyrene, and polyethylene. Typically, such apertures must first be treated with a solvent before application of a mixture of solvent and phospholipid to form a membrane. Preferably, ALBMs may be formed with little or no solvent from phospholipid monolayers by Langmuir-Blodgett techniques. See, for example Montal and Mueller, *Proc. Natl. Acad. Sci. USA*. 69:3561–3566 (1972); Montal, *Meth. Enzymol.* 32:545–556 (1974); and Lindstrom et al., *J. Biol. Chem.* 255:8340–8350 (1980).

Solvent-free ALBMs are very thin, being approximately as thick as the length of two phospholipid molecules laid end-to-end. Even solvent-containing artificial lipid bilayers, which may have a layer of solvent between the two phospholipid leaflets, are extremely thin. One method of determining whether a bilayer has been formed is to observe the disappearance of Newton's rings (colored patterns caused by interference between light reflected from each external surface of a thinning lipid membrane) as the membrane thins to a thickness less than that of a wavelength of visible light.

ALBMs are not as stable as membranes found in living cells. In living organisms, lipid bilayers form structures that may be as small as only a few nanometers to a few tens of nanometers in size. Although thin, artificial lipid bilayers usually have much more surface area than the bilayer membranes that surround living cells and intracellular organelles. In addition, ALBMs are formed across artificial apertures, which may have discontinuities and defects at the edges and surfaces and which are typically formed by manual processes which preclude uniformity of manufacture. Thus, ALBMs quite often rupture spontaneously within a few seconds or minutes after formation, possibly due to their relatively large surface area, imperfections in the apertures, and their lack of the small molecules, proteins and sugars found in living membranes which may enhance the membrane stability.

Biosensors are devices that utilize biomolecules to recognize target molecules in a highly specific manner. Biosensors are used commercially for sensing glucose, and are used in research and industrial applications to detect other molecules, often at extremely low concentrations. For example, enzymes are used to detect the presence of molecules that serve as substrates for a chemical reaction catalyzed by the enzyme. Ligand receptors are exquisitely sensitive to target molecules, often responding to the binding of a single target molecule. Ion channels may respond to ligand binding, to small voltage changes, to mechanical stress, or to other signals and so are also useful for detecting changes in their environment.

The biomolecules used as detectors in biosensors are typically membrane-bound or membrane-associated molecules derived from plant or animal cells. The activity of such molecules is quite often critically dependent upon the membrane with which they are associated or to which they are bound. In addition, where a biosensor depends upon a membrane-bound biomolecule as a sensor element, instability or rupture of the membranes destroys the sensor element. Accordingly, methods and devices for creating suitable membranes for use in biosensors are needed.

SUMMARY OF THE INVENTION

The invention provides methods for forming small apertures (termed "nanoapertures") under reproducible and controlled conditions, and provides devices and systems having nanoapertures. A device having a nanoaperture is termed a "nanoaperture chip. " Such microfabricated nanoaperture chips are suitable for a variety of uses, such as, for example, supporting artificial lipid bilayer membranes (ALBMs) for use in a biosensor. Nanoaperture chips may be combined with other features, such as electrodes, or electrodes, electrical power sources, and electronic sensing and amplifying circuitry, to provide biosensors and other devices.

Nanoapertures may have diameters ranging from as small as a few nanometers (nm) to as large as several millimeters (mm). More than one nanoaperture may be formed in a substrate. Where the substrate is interposed between two baths or other locations, the nanoaperture may serve as a conduit between the baths or locations. For example, a nanoaperture may be in contact with a chamber or a reservoir. A reservoir may contain a solution having peptides, proteins, small molecules, or other bioactive agents, such as neurotransmitters, hormones, ions, messenger molecules, nucleic acids, nucleic acid vectors, drugs, cells, cell fragments, cell organelles, liposomes, or other biologically active materials. The nanoaperture is effective to provide a conduit for the delivery of materials from one chamber to another, or for delivery of materials to a membrane formed across the nanoaperture.

A device having a nanoaperture may be used as a support on which to form ALBMs, and provides stable and reproducible membranes. Where a substrate includes more than one nanoaperture, each nanoaperture may support an ALBM so that substrates and devices may have multiple ALBMs. Such membranes may incorporate channels, receptors, or other molecules useful as biosensors, as voltage-sensitive gates or rectifiers, or as ligand-sensitive gates, so that the nanoapertures may be used in biosensing devices, circuit elements, and other biological, bio-electronic, or biochemical applications.

ALBMs containing biomolecules sensitive to target molecules may be used as sensors in biosensor devices; biosensors with multiple nanoapertures and multiple ALBMs may be sensitive to more than one target molecule, and, since multiple ALBMs provide back-up in case of rupture or other failure of an ALBM across a single nanoaperture, are more fault-tolerant than other biosensors.

Accordingly, in a first embodiment, the invention provides a silicon substrate with a nanoaperture that has a hydrophobic surface. The nanoaperture is a small aperture that may have a diameter of less than about 1 mm. In some embodiments, the nanoaperture diameter may be less than about 10 $\mu$m; in other embodiments, the nanoaperture diameter may be less than about 1 $\mu$m; and in still other embodiments, the nanoaperture diameter may be less than about 10 nm. A nanoaperture in any embodiment discussed previously or subsequently may have any suitable diameter of a size approximately within any of the preceding ranges. The silicon substrate may have an oxidized surface.

Silicon substrates embodying features of the invention may be hydrophobic surfaces having a plurality of nanoapertures. The silicon substrates with a plurality of nanoapertures may have oxidized surfaces.

In other embodiments, the invention provides devices including a silicon substrate having a nanoaperture and a hydrophobic surface. Devices embodying features of the invention may also include a silicon substrate having a nanoaperture, an oxidized surface and a hydrophobic surface. In further embodiments, the devices may include substrates having a plurality of nanoapertures.

In addition, the invention provides devices (e.g., biosensors) having silicon substrates having a hydrophobic surface, a nanoaperture or a plurality of nanoapertures, and an ALBM supported by a nanoaperture or a plurality of ALBMs supported by a plurality of nanoapertures. The silicon substrate of a devices with an ALBM may further have an oxidized surface.

The invention further provides systems comprising a device with a silicon substrate having a nanoaperture and a hydrophobic surface, and an ALBM; an electrode; and an operant electrical connection between said electrode and said device. The devices of the systems may further have substrates with oxidized surfaces.

In another embodiment, the invention provides methods for forming a nanoaperture in a silicon substrate, comprising the steps of growing a layer of silicon nitride on a silicon substrate with a surface; application of a photosensitive polymer to said surface; plasma etching said silicon surface; and anisotropically etching said surface with an anisotropic etchant. In an embodiment of the methods of the invention, the silicon surface may be perpendicular to the <100> direction. In another embodiment of the methods, the silicon surface may be perpendicular to the <111> direction. In yet another embodiment of the methods, the silicon surface may be perpendicular to the <110> direction. The anisotropic etchant may be tetramethylammonium hydroxide. In further embodiments, the methods may include the step of oxidizing the surface, such as by exposure of the surface to superheated steam. The methods may also include the step of altering the substrate surface so as to make said substrate surface hydrophobic, such as by soaking the silicon substrate in a solution containing an alkylsilane. The method may further comprise the step of applying a polymer, such as polyimide, to the substrate.

The invention also provides methods for forming an ALBM on a silicon substrate, comprising the steps of providing a hydrophobic silicon substrate with a front substrate surface, a back substrate surface, and an aperture separating said substrate surfaces; contacting the substrate surfaces with front and back solutions having lipid monolayers on the solution surfaces; and raising the solution surface levels above the aperture to cover said aperture. In embodiments of the method, the hydrophobic silicon substrate may be an oxidized hydrophobic silicon substrate, and the diameters of the nanoapertures may be any diameter as discussed previously. In further embodiments, the substrate may be treated with a solvent solution, such as one containing hexadecane, prior to formation of the ALBM.

The methods, devices and systems of the invention provide multiple advantages. Advantages over other silicon-based substrates include simplicity of design and the bilayer formation technique. The present methods for treating silicon substrates so as to provide hydrophobic silicon substrate surfaces and for forming nanoapertures in them provides for the use of the Langmuir-Blodgett technique for forming ALBMs on silicon substrates. ALBMs formed by the methods and with the devices of the invention are more stable and reproducible than membranes formed using prior techniques and devices. In addition, due at least in part to the greater control over the design and manufacturing of apertures and reservoirs, the present invention provides greater control over experimental parameters than prior methods and devices.

Figure 1A:
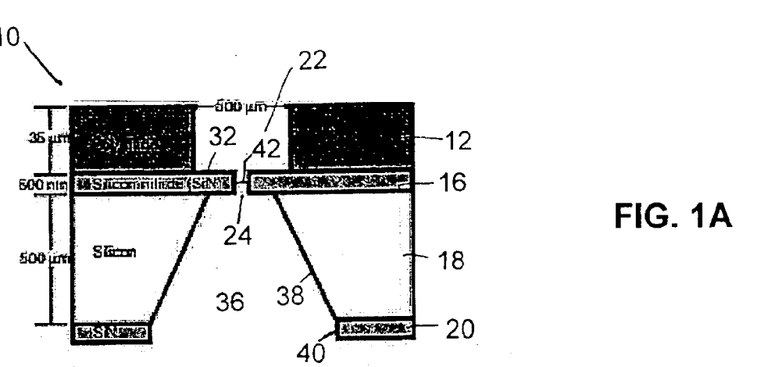
FIG. 1A shows a cross-section of a nanoaperture chip embodying features of the invention.
Figure 1B:
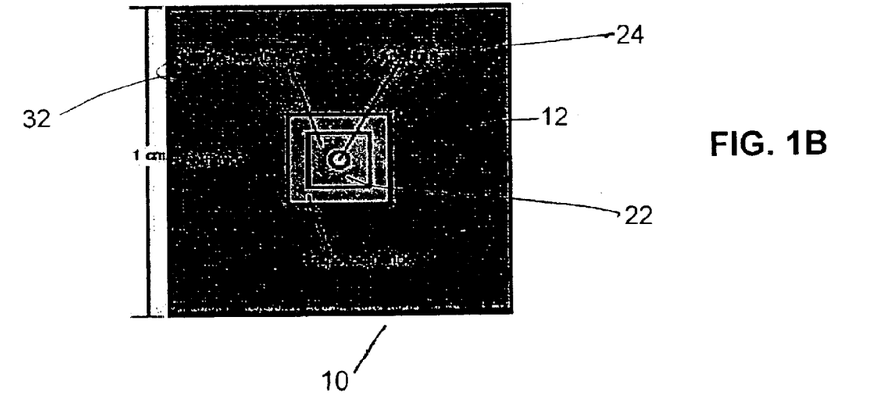
FIG. 1B is a top plan view of the nanoaperture chip of FIG. 1A.

DETAILED DESCRIPTION OF THE INVENTION nanoaperture chip 10 embodying features of the invention, having a nanoaperture formed by the methods of the invention, is shown in FIG. 1. FIG. 1A shows a perspective view, and FIG. 1B a plan view of the nanoaperture chip 10. In the orientation shown, the upper surface of the nanoaperture chip 10 includes the substrate 12, which may be made with any material or materials, preferably with materials compatible with bilayer formation. For example, glass, ceramic, silicon, silicon compounds and mixtures, polyimide, polystyrene, polyethylene, polylactide, Teflone® or other polymer, are suitable materials. The substrate 12 may be made from polymers such as polyimide or SU-8 (MicroChem Corporation, Newton Mass. USA). In preferred embodiments, substrate 12 includes polyimide.

Underlying the substrate 12 is a supporting layer 16. An intermediate layer 18, preferably formed with silicon, is provided adjacent to and below the supporting layer 16. A base layer 20 is shown lying below the intermediate layer 18, so that intermediate layer 18 is sandwiched between supporting layer 16 and base layer 20. In embodiments of the invention, supporting layer 16 and base layer 20 are formed with silicon nitride. Aperture 24, a hole through supporting layer 16, is a nanoaperture. The methods of the invention are effective to form nanoapertures as small as only a few nm to a mm in diameter.

Silicon and silicon nitride provide stable substrate and intermediate layers, and may be produced and formed with widely available tools and knowledge for fabrication. Techniques for silicon device production are highly reproducible and accurate at the sub-micron level. Additionally, silicon allows for greater control of aperture geometry and location, including the ability to create arrays of apertures.

The devices and methods of the invention may be used to support artificial bilayer membranes. Such membranes may incorporate channels, receptors, or other molecules useful as biosensors, as voltage-sensitive gates or rectifiers, or as ligand-sensitive gates, so that the nanoapertures may be used in biosensing devices, circuit elements, and other biological, bio-electronic, or biochemical applications.

The nanoaperture chip 10 shown in FIGS. 1A and 1B also has a recess 22 adjacent aperture 24. Recess 22 in the substrate 12 leads to an aperture 24 which forms a passage across the supporting layer 16. As shown in FIG. 1B, the floor 32 of recess 22 is formed of supporting layer 16 free of overlying substrate 12. Aperture rim 34, in supporting layer 16 surrounding aperture 24, defines the passageway through supporting layer 16. Aperture 24 opens into reservoir 36 defined by wall 38 of the intermediate layer 18 and wall 40 of the base layer 20. A membrane 42, such as a lipid bilayer membrane, may be formed across aperture 24 to separate reservoir 36 from recess 22.

A membrane 42, in place across aperture 24, may prevent substantially all passage of material between recess 22 and reservoir 36. However, membrane 42 may be a semipermeable membrane effective to regulate the passage of material through aperture 24 without completely preventing all passage of material. For example, membrane 42 may be an ALBM. An ALBM containing molecules such as ion channels or carriers is able to readily pass specific ions while restricting or substantially preventing the passage of other ions.

Recess 22 and reservoir 36 may each contain a solution; the solution in recess 22 may be the same or different from the solution in reservoir 36. Where bioactive agents such as ion channels, ligand receptors, and biosensing molecules are. incorporated into a lipid bilayer membrane, the solutions are preferably physiological solutions, such as a saline solution. Examples of such solutions include phosphate-buffered saline, bicarbonate-buffered saline, HEPES-buffered saline, and other saline solutions. Other suitable saline solutions, which include factors conducive to cell growth and proliferation, include Dulbecco's Modified Eagle's Medium (OMEM, Sigma Chemical Co., St. Louis Mo., Cat. #D6546), and other solutions known in the art.

The solutions may further contain bioactive agents 44, so that recess 22 and/or reservoir 36 contain bioactive agents which may thus have access to aperture 24 and membrane 42. For example, reservoir 38 may contain hormones, neurotransmitters in liposomes, cell homogenates, cell extracts, or intact cells.

Bioactive agents 44 may regulate the permeability of the membrane 42, or may be capable of contacting and fusing with membrane 42 effective to deliver agents to the recess 24 from the reservoir 36 or from the recess 24 to the reservoir 36. Delivery of bioactive agents may be used in the manufacture of a biosensor to provide biosensing molecules to a membrane 42. Bioactive agents 44 may include channel forming molecules, such as α-hemolysin, gramicidin, alamethicin, or other channel former; carrier molecules such as amphotericin; substances such as adhesion molecules, antibodies, dyes, and so forth. Bioactive agents 44 may be micelles, liposomes, or biological membrane preparations containing ion channels, receptors, or other biologically active molecules that may fuse with and insert molecules into membrane 42 or modulate its activity.

Figure 1C:
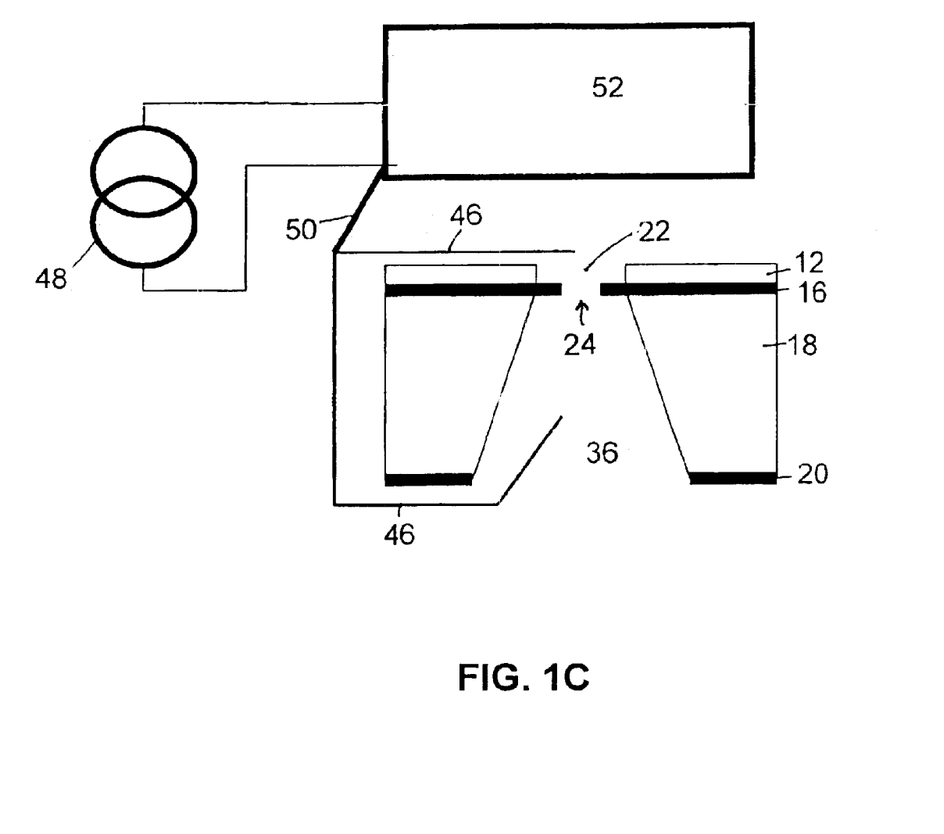
FIG. 1C is a system including a nanoaperture chip.

Also shown in FIG. 1C are electrodes 46. Electrodes 46 may be made from any of a variety of materials, including silver, silver chloride, chromium, tin, indium, indium tin oxide, zinc oxide, colloidal stamped carbon, platinum, palladium, gold, aluminum, and other elements, oxides and materials known in the art. Electrodes 46 may be used to carry electrical signals from power source 48 to supply current or impose a voltage between electrodes 46 and to regulate molecules associated with membrane 42 or to sense current or voltage changes caused by changes in membrane 42, as would occur when membrane-bound or associated bioactive molecules sensed target molecules. Connecting link 50 includes electrical conductors to connect power source 48 and controller 52 (which may include amplifiers and other electronic sensing, filtering and amplifying components) with electrodes 46. Electrodes 46, connecting link 50, controller 52, and other electronic components may be integral with or separate from nanoaperture chip 10.

The components and features necessary to construct devices such-as a nanoaperture chip 10 may be made using microfabrication techniques. For example, crystalline silicon may be machined by the use of chemical etchants, which etch silicon crystals at different rates in different directions. Anisotropic etchants, such as tetramethylammonium hydroxide (TMAH), potassium hydroxide (KOH) and ethylene diamine pyrocatechol (EDP) etch silicon much more slowly in the <111> direction than in the <100> and <110> directions. The etching rate in one direction may be as much as 100-fold higher than the etching rate in another direction. Grooves and holes through silicon substrates with walls perpendicular to the substrate surface may be formed by anisotropic etching of a <110> silicon substrate. Alternatively, anisotropic etching of a <100> silicon substrate to expose {111} planes forms flat surfaces oriented at an approximately 55° angle with the substrate surface. The sophisticated microstructures that may be constructed using such microfabrication methods may be used to make devices such as nanoaperture chips 10. The structures shown in the following figures were made using the Stanford Nanofabrication facility (Leland Stanford Junior University, Stanford, Calif. 94305).

Figure 2A:
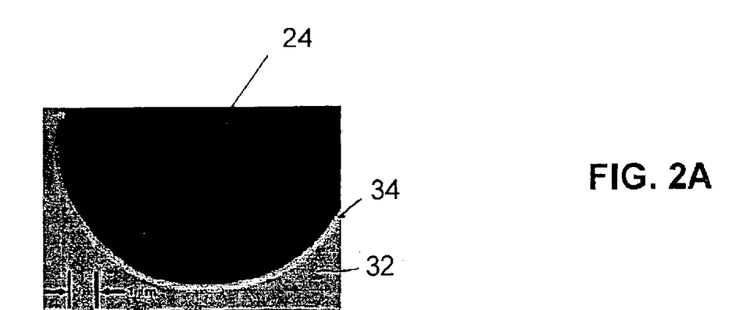
FIG. 2A is a plan view scanning electron micrograph (SEM) of a nanoaperture embodying features of the invention.

An aperture 24 formed in a silicon nitride supporting layer 16 of a nanoaperture chip 10 embodying features of the invention is shown in FIG. 2A. The view in FIG. 2A is in the same orientation as the view shown in FIG. 1B, showing the aperture 24 facing the upper surface of the nanoaperture chip 10. The aperture is approximately 10 μm in diameter (scale bar represents 1 μm). Aperture 24 is bounded by rim 34 in exposed floor 32 of recess 22. At the small scale shown in FIG. 2A, the aperture 24 is quite smooth, both in terms of shape and surface. To improve resolution, the device was first coated in gold. Note that the plasma etching used for this processing does not create vertical sidewalls in the aperture. The aspect ratio of the sidewalls is roughly 2.5:1. Although the example of the aperture 24 shown in FIG. 2A forms a passageway through a supporting layer 16 made from silicon nitride, other materials may also be used, such as polymers and glass.

A microfluidic reservoir 36 may be connected to the other side of recess 22. A reservoir 36 may be configured to be of a size able to contain neuromodulatory agents in aqueous solution or aqueous suspension. Aperture 24 is effective to provide a pathway between recess 22 and reservoir 36, which may be used as a conduit for the transfer of materials between recess 22 and reservoir 36, or to deliver materials to a membrane 42 formed across aperture 24.

Figure 2B:
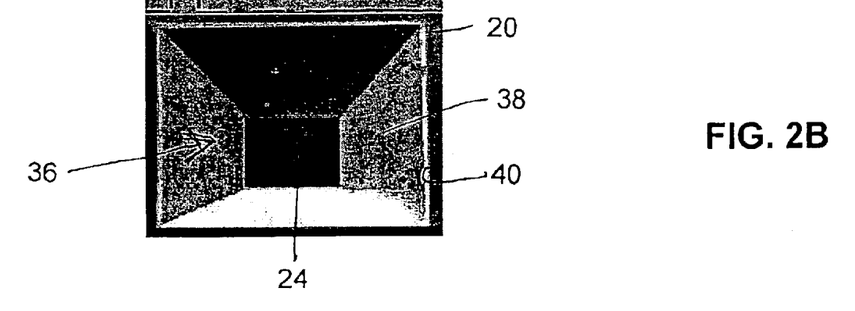
FIG. 2B is a plan view SEM of a reservoir of a nanoaperture chip embodying features of the invention.

FIG. 2B is a scanning electron micrograph (SEM) of a microfabricated well that has a microaperture in the bottom, showing reservoir 36 of a nanoaperture chip 10 embodying features of the invention, viewed from the face opposite to the substrate surface 12. Shown at a larger scale than FIG. 2A, this micrograph of the reservoir 36 viewed from the trans side of the nanoaperture chip 10 shows the smooth silicon nitride surface surrounding the aperture 24. Wall 38 of the intermediate layer 18 and wall 40 of the base layer 20 are shown, with a small amount of base layer 20 shown framing the walls 38 and 40. The black spot indicates the aperture 24 configured for cell attachment and stimulation (not clearly visible at this magnification). The reservoir 36 is designed for holding the culture solution for the cells. The size of the well is 1 mm across, narrowing to 180 μm near the aperture.

As shown in FIG. 1, the recesses 22 and reservoirs 36 of the devices of the present invention are suitable for the storage of bioactive agents, and for the delivery of bioactive agents to a membrane 42 formed across an aperture 24, or to any other object or material located at or across aperture 24. These agents may be free in aqueous solution or aqueous suspension, may be present in micelles, or may be carried by liposomes.

Liposomes, as is known in the art, are small membranous vesicles suitable for delivery of both hydrophilic and hydrophobic compounds. Pharmaceutical administration systems based on liposomes are described in, e.g., Gregoriadis, G. (editor) Liposome Technology, Vol. II, Incorporation of Drugs, Proteins and Genetic Material, CRC Press 1984, and in Knight, C. G. (editor). Liposomes: From Physical Structure to Therapeutic Applications, Elsevier 1981. Bioactive agents suitable for the practice of the invention further include biological membrane preparations containing ion channels, receptors, or other biologically active molecules, as described in, e.g., Coronado et al. J. Gen. Phys. 76:424–446 (1980). Such biological membrane preparations may fuse with and insert molecules into a membrane 42 across an aperture 24, or into the membrane of a cell 26, neurite 28 or growth cone 30. For example, gramicidin, alamethicin, and other molecules known in the art are suitable pore-forming molecules for the practice of this embodiment of the invention. Ion channel molecules suitable for the practice of the invention include multi-subunit macromolecule assemblies such as cyclic nucleotide-gated channels, calcium-sensitive channels, ligand-gated ion channels including ACHR ion channels, glutamate receptor ion channels, including all NMDA, AMPA, quisqualate, kainate subtypes, glycine receptor ion channels, and voltage-gated ion channel molecules and multi-subunit macromolecular assemblies such as sodium channels, potassium channels, calcium channels, chloride channels, and other channels, including gap junction channels, mechanosensitive channels, non-gated, and non-selective channels. Carrier molecules are other suitable bioactive agents. Alternatively, membranes may be formed with proteins, such as pore-formers and carriers, already incorporated as part of the membrane-forming material. See, e.g., Schindler, Methods Enzymol. (1989) 171:225–253.

Such nanoaperture chips with multiple nanoapertures may be used to support multiple ALBMs which may be used, for example, as biosensors. Where the ALBMs all contain the same biosensors, the sensitivity and amplitude of signal derived from the assembly is increased compared to the signal from a single artificial lipid bilayer membrane. In addition, multiple ALBMs provide fault tolerance because the loss of a single membrane across one of many nanoapertures due to rupture or other mishap does not completely destroy the usefulness of a device, such as a biosensor, of which the nanoapertures are a critical part. This is not true with devices having only a single artificial lipid bilayer membrane across a single nanoaperture. Nanoaperture chips and devices containing nanoaperture chips with multiple nanoapertures may have ALBMs having different bioactive molecules in different ALBMs, providing multiple biosensors and a wider range of biosensing capability than is possible with a single sensor. Similarly, where multiple ALBMs in a single substrate or a single device all contain the same bioactive molecules, different ALBMs may contain different amounts or different concentrations of these bioactive molecules to provide a range of sensitivity to the target molecules that is not possible with a single biosensor.

EXAMPLE 1

Microfabrication of Apertures

Microfabricated apertures on a silicon chip surfaces have been made using the Stanford Nanofabrication Facility. Microfabricated wells with microfabricated apertures are shown in FIG. 2. Silicon processing techniques were adapted for producing micrometer and nanometer-sized apertures in a silicon nitride membrane (large features and small features). Using low-pressure chemical vapor deposition (LPCVD), a thin layer (500 nm) of silicon nitride was grown on the surface of <100> orientation silicon wafers. A combination of lithography to define the structures in a photosensitive polymer was followed by plasma etching to pattern the structures in the silicon nitride-created apertures on one side of the wafer and an etchant masking layer on the other side. An anisotropic etchant, such as tetramethylammonium hydroxide (TMAH), was used to remove the silicon along the {111} crystal plane, but leave the silicon nitride unaffected. This produced a via hole (a connecting passageway) beneath the aperture, exposing the silicon nitride membrane and completing the processing.

In particular, standard contact photolithography and plasma etching of the silicon nitride defined the aperture (the small feature). The reservoir (the large feature) was defined using backside alignment, contact photolithography, and plasma etching was used (see FIG. 2B).

With the features defined in the silicon nitride, the wafers were placed in 20% TMAH at 100° C. for approximately 5 hours. The silicon nitride acted as a mask, allowing the TMAH to anisotropically etch through the wafer along the (111) crystal plane.

In order to reduce capacitance and noise that would arise because exposed silicon is conductive, the surface was oxidized with steam oxidation at 1100° C. for 4 hours, yielding ~1.1 $\mu$m of oxide. In order to reduce the capacitance, a photosensitive polyimide layer about 60 to about 70 nm thick was spun onto the surface, which was then exposed under a contact aligner, developed, and cured. This yielded a cured polyimide layer about 30 to about 35 nm thick.

In order to create a hydrophobic surface, the treated silicon wafers are soaked in a mixture of hexadecane, chloroform, and octyltrichlorosilane (80:19:1 v:v:v) for 15 minutes per side. Two rinses in chloroform for 5 minutes each completed the processing. The coating was tested by applying ~5 $\mu$m droplets of water and verifying that the contact angle was greater than 90°.

Bilayers were formed by the Langmuir-Blodgett technique. The aperture was first pretreated with ~5 ml of hexadecane in hexane (1:9 v:v). The treated wafer was mounted between two teflon baths with silicone vacuum grease. Each bath was filled with 1M KCl to just below the aperture. A solution of 5 ml at 10 mg/ml of 1,2-diphytanoyl-sn-glycerophosphocholine (Avanti Polar Lipids, Birmingham, Ala.) in chloroform was applied to each bath and allowed to evaporate. The solution level was then raised, forming an ALBM across the aperture. Formation of an ALBM was verified by measurements of the capacitance and conductance between the two baths Shown in FIG. 2A is a SEM of the microfabricated container. Note the black spot indicated by the arrow is the microetched aperture adapted for cell attachment and stimulation. The well was designed for holding the culture solution for the cells. The size of the well is 1 mm across at its largest, narrowing to 180 $\mu$m. FIG. 2B shows the microaperture in the bottom of the container shown in FIG. 2A. The microaperture is approximately 10 $\mu$m in diameter. Although not shown, the other side of the aperture is connected to a microchannel reservoir that is made by sealing a PDMS stamp with microchannels to the underside of this substrate.

The conduit, or via, opens into a microfluidic channel that serves as a reservoir for neuromodulatory agents that may be applied to cells adherent to the substrate. The microfluidic channel was made from a standard PDMS stamp as described above and sealed to the wafer. Such a microfluidic channel can be readily sealed to the wafer with excellent sealant properties. The microfluidic channel described has wide ranging ramifications for use including (1) acting as general purpose buffer reservoir for constant replenishing/exchanging waste products from the other side of the cell (2) delivery of transmitters, liposomes, voltage/current clamping of the cell, or (3) for sampling released products from the cell.

Nanoapertures may be formed in sizes ranging from a few nm to a few mm and ALBMs may be formed across such nanoapertures.

EXAMPLE 2

Device Fabrication and Optimization

This Example describes the manufacture and optimization of devices embodying features of the invention for use in forming bilayer membranes across the microfabricated apertures of the devices. Nanoaperture chips were made with surface areas of about 1 cm$^2$ and with a final thickness of roughly 0.5 mm. Circular apertures of 25 $\mu$m through 250 $\mu$m (diameter) were plasma etched in 500 nm thick silicon nitride. The chips were covered in a thick polyimide, except for a square region of exposed silicon nitride 500 $\mu$m on a side.

Fabrication was done at the Stanford Nanofabrication Facility (SNF) with 4 inch, <100> orientation, boron-doped, double-polished silicon wafers, nominally 500 $\mu$m thick. Using low-pressure chemical vapor deposition (LPCVD), a thin layer (500 nm) of silicon nitride was grown on the surface of the wafers. Standard contact photolithography and plasma etching of the silicon nitride was used to define the small features (e.g., the apertures). The larger features on the backside of the wafer were similarly defined using backside alignment, contact photolithography, and plasma etching.

The silicon was etched anisotropically along the {111} plane at an angle of 54.7° to the wafer surface. The square hole in the backside of the wafer was chosen to yield a square 180 $\mu$m larger than, and centered on, the aperture. This left a thin silicon nitride membrane freely spanning the region without any silicon support. Because of the high tensile strength of silicon nitride, this nitride membrane was quite strong and stable, and was able to readily withstand the forces generated during processing.

With the features defined in the silicon nitride, the wafers were placed in 20% tetramethylammonium hydroxide (TMAH) at 100° C. for approximately 6 hours. The silicon nitride acted as a mask, allowing the TMAH to etch anisotropically through the wafer along the {111} crystal plane.

Since the exposed silicon is conductive, it was necessary to oxidize the surface to reduce capacitance and noise. This was accomplished with a steam oxidation at 1100° C. for 4 hours, providing ~1.1 $\mu$m of oxide. Finally, to reduce the capacitance further, a photosensitive polyimide (Durimide 7520, Arch Chemicals, Zwijndrecht, Belgium) was spun on 30–70 $\mu$m thick, exposed under a contact aligner, developed, and cured, yielding a coating 15–35 $\mu$m thick.

To create a hydrophobic surface, the chips were then soaked in a mixture of hexadecane (Sigma, St. Louis, Mo.), chloroform, and octyltrichlorosilane (Aldrich, Milwaukee, Wis.) in a ratio 80:19:1 (by volume) for 15 minutes per side. Two rinses in chloroform for 5 minutes each completed processing. The coating was tested by applying ~5 $\mu$l droplets of water and verifying that the contact angle was greater than 90°.

One advantage of silicon is the ability to control the thickness of the bilayer supporting partition (BSP). The thickness of the silicon nitride BSP was chosen to be an order of magnitude smaller than Teflon® partitions used to form apertures for bilayer formation (6–25 µm), with the expectation that thinner partitions provide a smaller solvent torus and a larger bilayer area. The partition is still a couple of orders of magnitude larger than a 2–nm thick bilayer, so bending of the lipids from the edges of the partition to the bilayer is still necessary. However, this bending distance is smaller, yielding a larger bilayer area relative to the aperture size. The impact of this upon stability is unknown, but it does allow more area for protein insertion and the ability to create bilayers across smaller apertures.

A nanoaperture chip with a membrane having bioactive molecules is to able to support an artificial lipid bilayer membrane and to make of sensitive electrical measurements of current flowing through and voltage across an ALBM. As with any electronic circuit, excessive capacitance may present a problem by increasing electrical noise. Excessive capacitance is a problem for two reasons: (1) electrical noise due to the access resistance in series with this capacitance, and (2), where a lipid bilayer is to be made across the nanoaperture, the inability to observe the membrane capacitance over the background. Since silicon is a conductor at room temperature, any contact of the bath to the silicon effectively connects the entire area of the chip to the system. A 1 cm$^2$ chip with 500 nm of silicon nitride ($\epsilon$=7.5) has a capacitance of 13 nF, three orders of magnitude greater than the capacitance of a 25 µm diameter bilayer.

However, a thin BSP in a solution containing chargecarriers has a large capacitance, which may present a problem where precise electrical measurements or precise electrical stimulation of a cell are desired. The solution to this problem was found to be two-fold. First, to remove the electrical connection between the silicon and bath, the wafers were exposed to steam at 1100° C., yielding just over a micron of oxide on all exposed silicon surfaces. This reduced the capacitance by a factor of two, since the system effectively becomes two nitride capacitors in series connected by a silicon conductor. It does, however, simplify the capacitative model of the system by removing discontinuities that would occur as the bath contacts the silicon.

Second, capacitance was reduced by addition of a polyimide layer. A negative, photosensitive polyimide ($\epsilon$=3.5) was chosen that can be processed using standard lithography. An application of 30 to 100 µm of polyimide becomes 15 to 50 µm when cured. In addition, the cured polyimide is highly resistant to solvent degradation. The design leaves 500 µm by 500 µm of nitride uncovered over the aperture. Manipulation of the solution level so that only 5 mm by 5 mm of the chip was exposed to solution reduced the capacitance from 35 µm of polyimide to only 22 pF.

EXAMPLE 3

Substrates with Multiple Nanoapertures

The techniques described in the previous example may also be used to produce silicon substrates having more than one nanoaperture. Multiple nanoapertures may be formed within a single recess on a substrate, or multiple assemblies each having a single or multiple nanoapertures within a single recess may be formed on a substrate.

A 4 inch, <100> orientation, boron-doped, doublepolished silicon wafer, nominally 500 µm thick, was used to form a nanoaperture chip having multiple nanoapertures within a single recess. Using low-pressure chemical vapor deposition (LPCVD), a thin layer (500 nm) of silicon nitride was grown on the surface of the wafer. Standard contact photolithography and plasma etching of the silicon nitride was used to define the small features (e.g., the apertures). One hundred twenty one 5 µm nano-apertures were formed in the wafer, in a square pattern having eleven nanoapertures on a side with the nanoapertures spaced 100 µm apart. The larger features on the backside of the wafer were similarly defined using backside alignment, contact photolithography, and plasma etching.

The silicon was etched anisotropically along the {111} plane at an angle of 54.7° to the wafer surface. The square holes in the backside of the wafer were chosen to yield a square larger than, and centered on, the array of nanoapertures. This left a thin silicon nitride membrane freely spanning the nanoaperture array region without any silicon support. Because of the high tensile strength of silicon nitride, these nitride membranes were quite strong and stable, and were able to readily withstand the forces generated during processing.

With the features defined in the silicon nitride, the wafers were placed in 20% tetramethylammonium hydroxide (TMAH) at 100° C. for approximately 6 hours. The silicon nitride acted as a mask, allowing the TMAH to etch anisotropically through the wafer along the {111} crystal plane. Oxidation of the surface in order to reduce capacitance and noise was accomplished with steam oxidation at 1100° C. for 4 hours, providing~1.1 µm of oxide. Finally, to reduce the capacitance further, a photosensitive polyimide (Durimide 7520, Arch Chemicals, Zwijndrecht, Belgium) was spun on to a thickness of about 30–70 µm, exposed under a contact aligner, developed, and cured to yield a coating of about 15–35 µm thick.

In order to create a hydrophobic surface; the chips were next soaked in a mixture of hexadecane (Sigma, St. Louis, Mo.), chloroform, and octyltrichlorosilane (Aldrich, Milwaukee, Wis.) in a ratio 80:19:1 (by volume) for 15 minutes per side. Two rinses in chloroform for 5 minutes each completed the processing. The coating was tested by applying ~5 µl droplets of water and verifying that the contact angle was greater than 90°.

EXAMPLE 4

Bilayer Formation Across Silicon Nitride Apertures

Lipid bilayers were formed by the method of Montal and Mueller (1972). In practicing the Langmuir-Blodgett technique, one raises two lipid monolayers across an aperture, allowing the lipids to align their hydrophobic tail portions across the aperture so as to form a lipid bilayer. Because of the hydrophobic nature of the lipid tails, in order to form stable bilayers the surface of a BSP must also be hydrophobic. If the substrate is hydrophobic, the lipids can smoothly transition from coating the substrate to spanning the aperture. To reverse the wetting properties of the naturally hydrophilic silicon nitride, the silicon nitride was coated with an alkylsilane (octyltrichlorosilane). Application of this coating was quite simple and very effective. It was not found to be possible to form a bilayer with untreated devices. Use of longer carbon chain silanes or alternativematerials to make the surface even more hydrophobic would further increase bilayer stability.

The characteristics of the devices are shown in Table 1. The thickness of the polyimide was varied to verify our background capacitance model for the chips. The model is based upon our chambers, where the baths contact 5 mm by 5 mm of chip. The intrinsic capacitance of the baths and amplifier was measured to be 7.2 pF, and is included in this number. For a 50 μm aperture device, where the polyimide is 32 μm thick, the model yields a background capacitance of 45 pF, compared to 77 pF for 6 μm thick Teflon®.

Table 1. Characteristics of the devices used in this study. The polyimide thickness and total capacitance are measured, while the other properties are calculated.

| Aperture Size (μm) | Polyimide Thickness (μm) | Chip Background Capacitance (pF) | Total Capacitance (pF) | Bilayer Capacitance (μF/cm$^2$) | Expected Noise (pA) |
|---|---|---|---|---|---|
| 25 | 9.6 | 100.1 | 103.4 +/− 1.8 (n = 6) | 0.67 +/− 0.36 | 3.4 |
| 50 | 32.1 | 45.0 | 57.7 +/− 2.1 (n = 10) | 0.65 +/− 0.11 | 1.4 |
| 75 | 19.8 | 60.6 | 91.1 +/− 2.0 (n = 9) | 0.69 +/− 0.04 | 1.8 |
| 100 | 17.5 | 66.4 | 117.4 +/− 1.1 (n = 2) | 0.65 +/− 0.01 | 2.0 |
| 150 | 21.7 | 59.4 | 182.6 +/− 5.3 (n = 6) | 0.70 +/− 0.03 | 2.6 |
| 250 | 19.6 | 65.9 | 379.8 +/− 6.3 (n = 5) | 0.64 +/− 0.01 | 4.4 |

The bilayer specific capacitance was determined simply by dividing the difference between the measured total capacitance and the calculated background capacitance by the area of the aperture. This number is in the range of 0.64 to 0.70 μF/cm$^2$ and corresponds well with that found in other artificial bilayer experiments. The total capacitance was measured within a few minutes after bilayer formation to avoid changes due to bilayer thinning. Note that as the aperture area decreased, the bilayer capacitance became quite small compared to the background, yielding a large error in the specific capacitance.

The empirical evidence for the formation of a bilayer on any nanoaperture chip was threefold. For the largest size apertures, the change in capacitance due to the bilayer was readily observable. For a typical specific capacitance value of 0.65 μF/cm$^2$, a bilayer on a 100 μm aperture would have a capacitance of 51 pF, which is easily observed over a 65 pF background. In addition, a resistance through the aperture grater than 1 GΩ indicates the presence of a bilayer. For all aperture sizes, a "gigaseal" of at least 2.5 GΩ was observed, indicating the formation of a bilayer.

For smaller apertures, it was more difficult to observe the capacitance change the background. In this case, membrane-bound proteins that affect the electrical properties of the bilayer, such as carriers and ion channels, offered the best proof of the formation of a bilayer. The ion channel peptide Gramicidin D (gD), was chosen for ease of use and large conductance change. A lipid bilayer membrane is required in order for Gramicidin D to increase current flow. After adding 5 to 20 μl of 2 mg/ml gD (Sigma, St. Louis, Mo.) in ethanol to each bath, the conductance of the bilayer dramatically increased within minutes, while the capacitance remained constant. The addition of ethanol by itself had no effect. Thus, the increase in current flow in response to an applied potential (measured by an increase in conductance) indicated that a true lipid bilayer had been formed.

Observing current flow carried by individual ion channels or pores across a membrane requires that the electrical noise to be as small as possible. In addition to environmental sources and capacitative noise, there are two major sources of electrical noise: photocarriers in the silicon, and access resistance. The first noise source, light, is produced when light incident upon the chip excites carriers across the band gap, creating a fluctuating charge between the two layers of nitride. Depending on the source and intensity of light, the noise produced may measure tens to hundreds of picoamperes peak-to-peak. Simply shutting off room lights or enclosing the setup in a light proof box was sufficient to reduce the electrical noise contributed by this noise source.

The other source of electrical noise was due to the access resistance of the baths in series with the bilayer capacitance. The total access resistance ($R_a$) contains three components: the bulk bath resistivity (32 Ω-cm), the bath resistivity in the aperture, and the access resistance to the aperture. For a small access resistance, the expected noise in amperes rms was $\sqrt{4kTR_a(2\pi f^2 C^2)}$ where f is the measurement bandwidth.

The results of this calculation for each tested chip are shown in Table 1. For the 50 μm aperture, the expectation from this calcuation was 1.4 pA rms, while the actual measured values were between 1.8 pA and 2.4 pA. The difference was attributed to local environmental noise.

EXAMPLE 5

Bilayer stability and lifetime

Figure 3A:
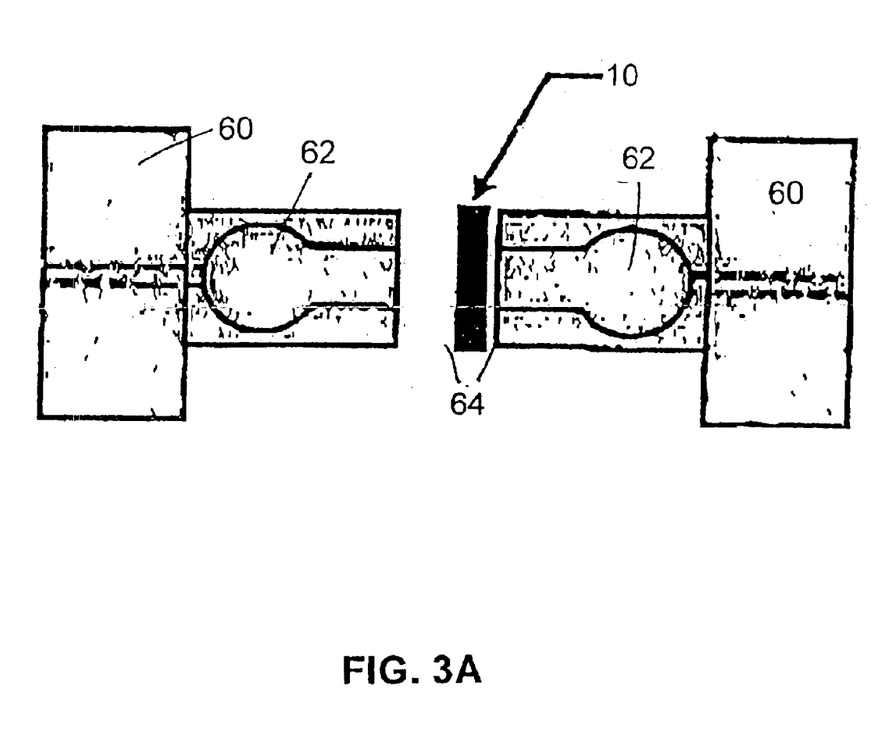
FIG. 3A is a plan view of a bilayer assembly including a substrate with a nanoaperture.

Bilayers were formed by the technique of Montal and Mueller (1972). A bilayer chamber was assembled by placing a nanoaperture chip 10 with a single nanoaperture between two shaped Teflon® blocks 60 to form a partition between two baths 62 created by cavities formed in the blocks. A schematic diagram of the assembled bilayer chamber is shown in FIG. 3. Silicone high vacuum grease (Dow Corning, Midland, Mich.) was used to seal the junctions 64 between the nanoaperture chip 10 and the Teflon® blocks 60. The aperture was first pretreated with ~5 μl of 1:9 (v:v) hexadecane:hexane (Burdick & Jackson, Muskegon, Mich.). Each bath was filled with 1 M KCl to just below the aperture. A solution of 5 μl at 10 mg/ml of 1,2-diphytanoyl-sn-glycerophosphocholine (Avanti Polar Lipids, Alabaster, Ala.) in chloroform was applied to each bath and allowed to evaporate. When the water level in each bath was raised, a lipid bilayer formed across the aperture, as evidenced by the capacitance and conductance of the device.

The ability to support the formation of a bilayer that will be stable for an extended period of time is an important property for any supporting substrate. Lipid bilayer membranes formed across the nanoapertures were found to be very stable. Nanoapertures were found to have two advantages over Teflon® partitions in terms of stability. First, lipid bilayer membranes formed on nanoapertures were not only thinner than those formed on Teflon® partitions, but are also more rigid. Teflon® partitions flex under changes in pressure, whereas nitride is comparatively inflexible. Second, the nitride surface and aperture edge are smooth at the nanometer level (see FIG. 2), unlike mechanically formed apertures in Teflon® partitions, which have micron-scale defects along the aperture edge.

Membrane stability was demonstrated by observing lipid bilayer membrane lifetime. Roughly half of the bilayers broke within the first few minutes, but some were stable for much longer. The longest bilayer lifetime observed was 8 hours. No attempts to measure systematically for longer than this time scale were made.

Figure 3B:
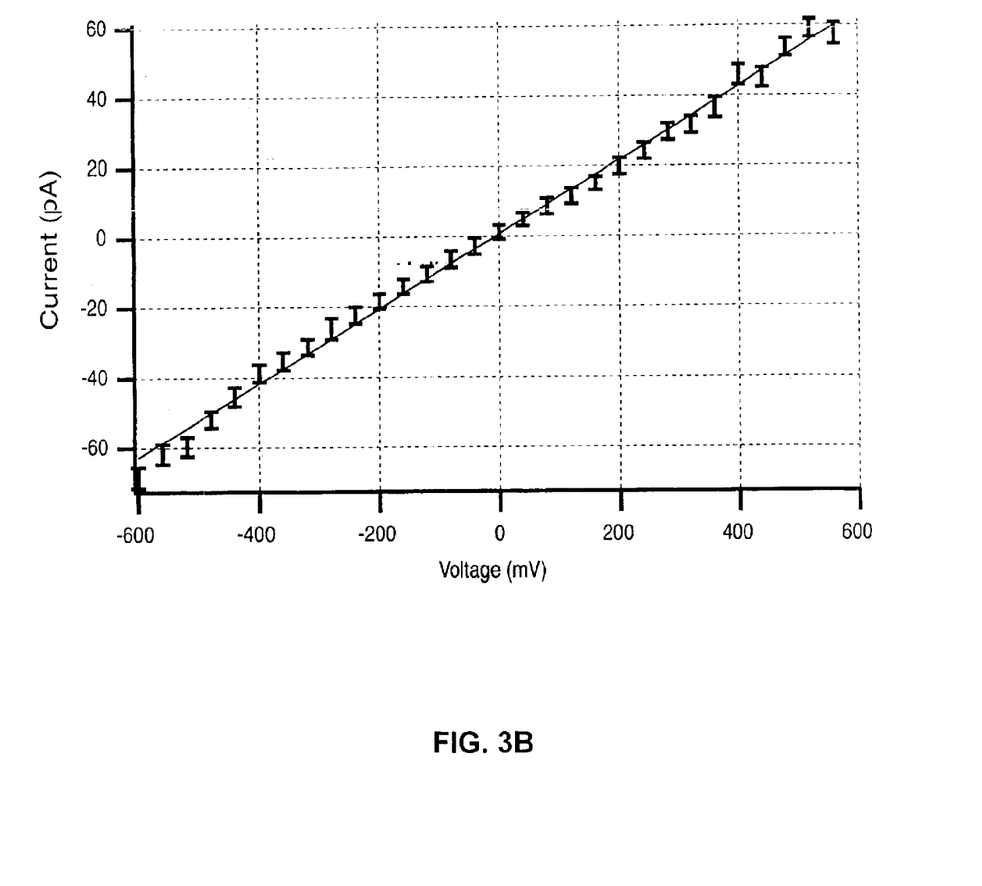
FIG. 3B is a current-voltage relation for a bilayer formed across an aperture on a nanoaperture chip.

Significantly, bilayers formed on nanoaperture chips were able to withstand relatively high transmembrane potentials. It is known that bilayers exhibit instabilities about 50 mV to about 100 mV below the electroporation threshold, at which bilayers irreversibly break. The electroporation threshold varied from device to device and bilayer to bilayer, but has been measured at over 800 mV. FIG. 3B shows a current-voltage relation from a bilayer formed across a 25 μm aperture in a nanoaperture chip. The slope of the relation corresponds to a bilayer resistance of 9.5±0.1 GΩ. In general, bilayers containing exogenous molecules, such as pore-formers, are found to be less stable than lipid bilayers without such molecules. Stable recordings over voltage ranges of ±480 mV in membranes containing pore-forming molecules have repeatedly been made.

It was found that the number of stable bilayers that were formed depended heavily on the cleanliness of the chip. It was rather easy to form a stable bilayer membrane using a fresh device with a nanoaperture that had just completed processing. However, it was more difficult to form a stable bilayer membrane across a nanoaperture that was reused after cleaning. Lipid bilayer membrane formation was found to be impossible following use of a cleaning process that left a residue across the nanoaperture.

EXAMPLE 6

Single-channel recordings with α-hemolysin

Ion channel activity due to staphylococcal α-hemolysin (αHL) channels was studied in lipid bilayer membranes formed across nanoapertures. This 293-amino acid heptameric pore forms 2 nm channels through the lipid bilayer. Single-channel recordings were performed with a patch clamp amplifier (Heka EPC-8, Heka Elektronik, Lambrecht, Germany) and an analog-to-digital converter (Instrutech ITC-18, Port Washington, N.Y.) sampled at 10 kHz. Filtering was performed with a built-in 7-pole low-pass Bessel filter at 5 kHz. The data was collected on computer using Pulse 8.4 (Heka) and analyzed with Igor Pro 4.0 (WaveMetrics, Lake Oswego, Oreg.). The αHL pores were added to the cis chamber (1 to 10 μl at 321 ng/ml), and held at −40 mV (trans side grounded). Addition of αHL to the trans side also yielded channels, but the diffusion time was longer due to the relatively long, narrow cavity.

Figure 4A:
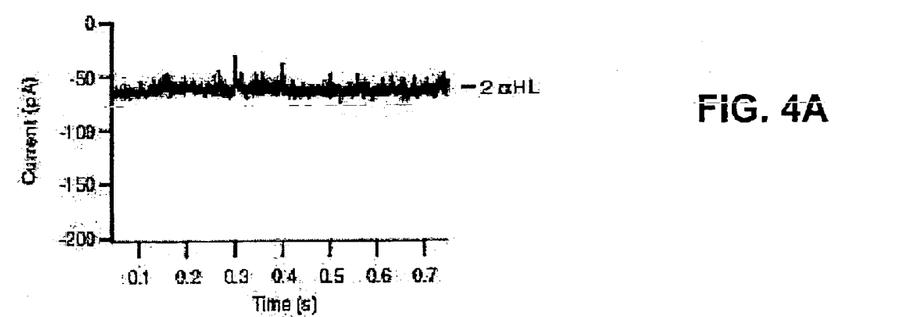
FIG. 4A is a representation of the measured current flow through an artificial bilayer membrane formed across a nanoaperture embodying features of the invention, with current shown along the vertical axis and time along the horizontal axis.
Figure 4B:
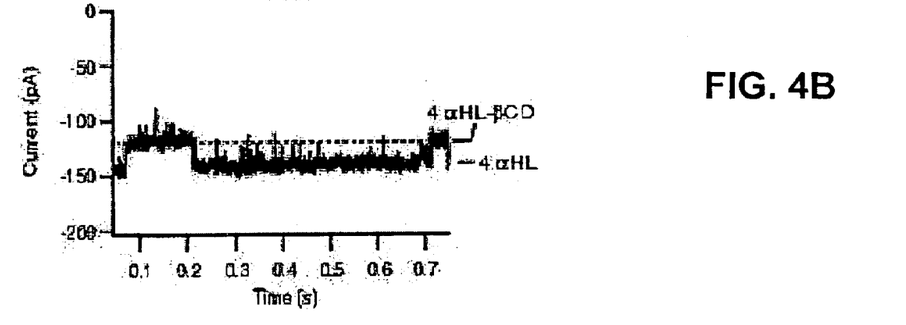
FIG. 4B is a representation of the measured current flow through an artificial bilayer membrane formed across a nanoaperture embodying features of the invention, with current shown along the vertical axis and time along the horizontal axis, after addition of α-hemolysin to the solution contacting the membrane.

FIGS. 4A and 4B illustrate single-channel currents recorded from artificial bilayer membranes across 100 μm apertures in microfabricated devices exposed to αHL. Shown in FIG. 4A are representative single-channel data for αHL channels. Voltage pulses of −40 mV were applied for 750 ms, and the current was recorded (31.0±3.2 pA per channel). Measurements at applied potentials greatly in excess of ±40 mV were also applied. The pore conductance of 811±55 pS demonstrated in this experiment is typical for αHL channels.

Figure 4C:
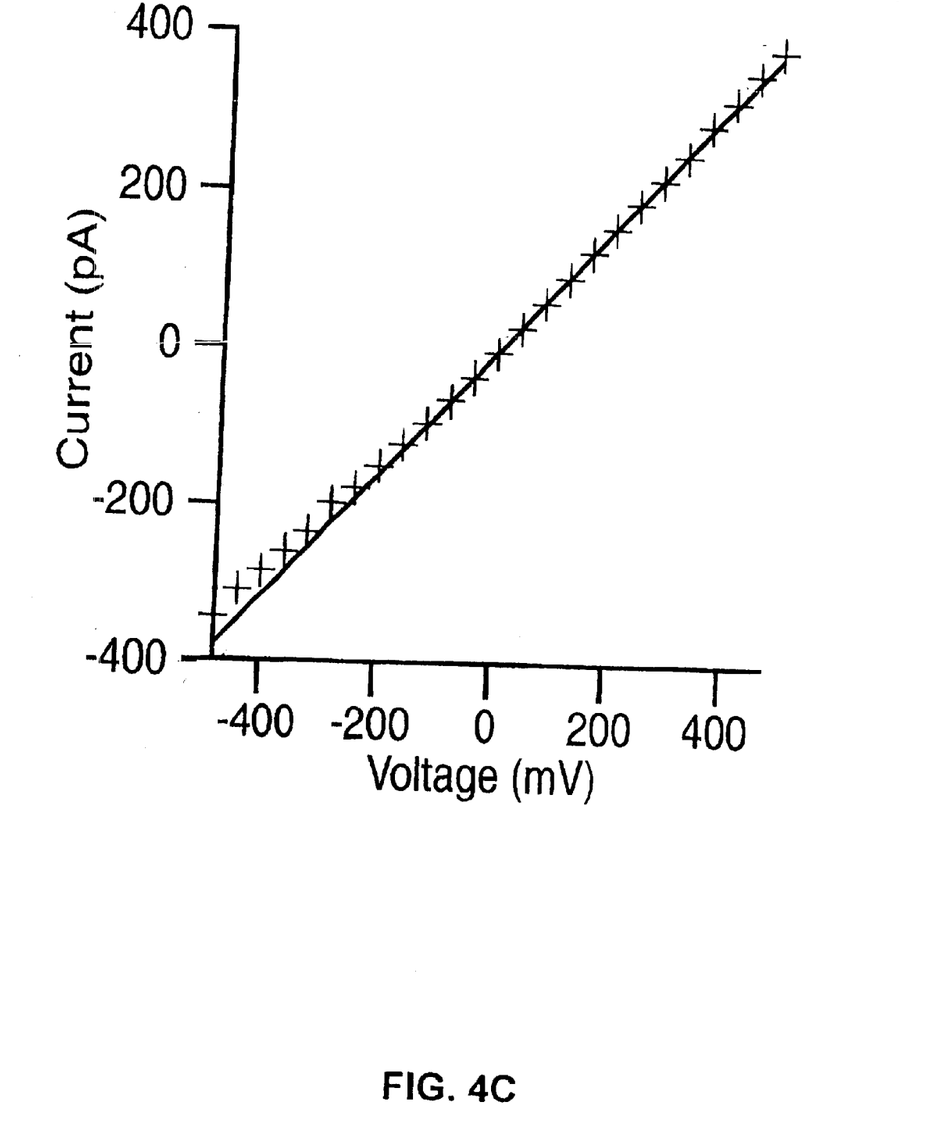
FIG. 4C is a current-voltage relation for αHL channels in a bilayer formed across an aperture in a nanoaperture chip.

An additional demonstration of the functionality of the αHL was accomplished with β-cyclodextrin (βCD), which inserts reversibly in the trans side of the channel. At micromolar concentrations (40 μM to 300 μM), βCD causes fluctuations in the current flow through the channel as the molecules move in and out of the protein. When a channel becomes blocked, a clearly observable 70±4% current reduction occurs. Shown in FIG. 4B are fluctuations due to βCD blocking the channels. There are four channels in the bilayer, with βCD blocking a channel at approximately 75 and 700 ms. Two such events are demonstrated in FIG. 4B occurring at roughly 75 and 700 ms from time zero. These results were in agreement with previous results for such channel recordings obtained with bilayers formed across Teflon® partitions. A current-voltage relation showing current flowing through for αHL channels in a bilayer across an aperture in a nanoaperture chip for potentials up to ±480 mV is shown in FIG. 4C.

What is claimed is:

1. A method for forming an artificial lipid bilayer membrane at a nanoaperture on a silicon substrate, comprising:
   providing a silicon substrate including a hydrophobic surface and a nanoaperture; and
   providing an artificial lipid bilayer membrane at said nanoaperture and in contact with said hydrophobic surface.

2. The method of claim 1, wherein said providing a silicon substrate comprises:
   growing a layer of silicon nitride on a first surface of said silicon substrate;
   applying a photosensitive polymer to said silicon nitride layer and to a second surface of said silicon substrate;
   plasma etching said silicon nitride to form said nanoaperture having a diameter of less than about 1 mm;
   anisotropically etching said second surface with an anisotropic etchant to form a reservoir communicating with said nanoaperture; and
   altering said silicon nitride layer effective to make said silicon nitride layer hydrophobic.

3. The method of claim 2, wherein said first silicon surface is a surface of <100> orientation silicon.

4. The method of claim 2, wherein said first silicon surface is a surface of <111> orientation silicon.

5. The method of claim 2, wherein said first silicon surface is a surface of <110> orientation silicon.

6. The method of claim 2, wherein said anisotropic etchant is tetramethylammonium hydroxide.

7. The method of claim 2, further comprising the step of oxidizing said silicon substrate after said anisotropically etching.

8. The method of claim 7, wherein said oxidizing step comprises exposure of said silicon substrate to super-heated steam.

9. The method of claim 8, wherein said super-heated steam has a temperature of about 1100° C.

10. The method of claim 2, wherein said altering comprises contacting said silicon nitride layer with an alkylsilane-containing solution.

11. The method of claim 10, wherein said alkylsilane-containing solution comprises octyltrichlorosilane.

12. The method of claim 2, further comprising the step of applying a polymer to said reservoir.

13. The method of claim 12, wherein said polymer is polyimide.

14. The method of claim 1, wherein said silicon substrate has a front surface and a back surface, said nanoaperture communicating with said surfaces, and wherein said providing an artificial lipid bilayer membrane comprises:
   contacting said front and back surfaces with front and back solutions, said front and back solutions having upper surfaces and having lipid monolayers on said upper surfaces;

whereby an artificial lipid bilayer membrane is formed at said nanoaperture.

15. The method of claim 14, wherein said hydrophobic silicon substrate is an oxidized hydrophobic silicon substrate.

16. The method of claim 14, wherein said nanoaperture has a diameter of less than about 100 µm.

17. The method of claim 14, wherein said nanoaperture has a diameter of less than about 1 µm.

18. The method of claim 14, wherein said nanoaperture has a diameter of less than about 100 µm.

19. The method of claim 14, further comprising treating said nanoaperture with a solvent solution.

20. The method of claim 19, wherein said solvent solution comprises hexadecane.

21. A device comprising a silicon substrate including a plurality of nanoapertures, a hydrophobic surface, and an artificial lipid bilayer membrane at one of said nanoapertures and in contact with said hydrophobic surface.

22. The device of claim 21, wherein said device is a biosensor.

23. A system comprising:
   a. a device comprising a silicon substrate including a nanoaperture and a hydrophobic surface, and an artificial lipid bilayer membrane at said nanoaperture and in contact with said hydrophobic surface;
   b. an electrode; and
   c. an operant electrical connection between said electrode and said device.

24. A silicon substrate including a nanoaperture, a hydrophobic surface, and an artificial lipid bilayer membrane at said nanoaperture and in contact with said hydrophobic surface.

25. The silicon substrate of claim 24, further comprising an oxidized surface.

26. The silicon substrate of claim 24, wherein said nanoaperture has a diameter less than about 1 mm.

27. The silicon substrate of claim 26, wherein said nanoaperture diameter is less than about 10 µm.

28. The silicon substrate of claim 26, wherein said nanoaperture diameter is less than about 1 µm.

29. The silicon substrate of claim 26, wherein said nanoaperture diameter is less than about 10 µm.

30. A silicon substrate including a hydrophobic surface, a plurality of nanoapertures and a plurality of artificial lipid bilayer membranes, wherein at least one of said membranes is at one of said nanoapertures and in contact with said hydrophobic surface.

31. The silicon substrate of claim 30, further comprising an oxidized surface.

32. The silicon substrate of claim 30, wherein a nanoaperture has a diameter less than about 1 mm.

33. The silicon substrate of claim 32, wherein a nanoaperture diameter is less than about 10 µm.

34. The silicon substrate of claim 32, wherein a nanoaperture diameter is less than about 1 µm.

35. The silicon substrate of claim 32, wherein a nanoaperture diameter is less than about 10 µm.

36. A device comprising a silicon substrate including a nanoaperture and a hydrophobic surface, and an artificial lipid bilayer membrane at said nanoaperture and in contact with said hydrophobic surface.

37. The device of claim 36, further comprising an oxidized surface.

38. The device of claim 36, wherein said device is a biosensor.

39. The device of claim 36, wherein said nanoaperture has a diameter less than about 1 mm.

40. The device of claim 39, wherein said nanoaperture has a diameter less than about 10 µm.

41. The device of claim 39, wherein said nanoaperture has a diameter less than about 1 µm.

42. The device of claim 39, wherein said nanoaperture has a diameter less than about 10 µm.

* * * * *